United States Patent [19]

Lai et al.

[11] Patent Number: 4,698,446

[45] Date of Patent: Oct. 6, 1987

[54] SYNTHESIS OF POLYAMINES AND MIXTURE FORMED THEREBY, OF DIPRIMARY POLYALKYLENE POLYAMINES WITH DISUBSTITUTED N-ADJACENT TERMINAL CARBON ATOM(S)

[75] Inventors: John T. Lai, Broadview Heights; Pyong N. Son, Akron, both of Ohio

[73] Assignee: The BF Goodrich Company, Akron, Ohio

[21] Appl. No.: 880,845

[22] Filed: Jul. 1, 1986

[51] Int. Cl.$^4$ .............................................. C07C 85/11
[52] U.S. Cl. .................................. 564/494; 564/422; 564/448; 544/402
[58] Field of Search ...................... 564/494, 422, 448; 544/402

[56] References Cited

U.S. PATENT DOCUMENTS

| | | | |
|---|---|---|---|
| 3,594,419 | 7/1971 | Rosenthal | 564/494 |
| 3,801,640 | 4/1974 | Knifton | 564/448 X |
| 3,923,893 | 12/1975 | Gates et al. | 564/494 |
| 4,159,996 | 7/1979 | Loue et al. | 564/494 X |
| 4,287,365 | 9/1981 | Becker et al. | 564/422 |
| 4,454,331 | 6/1984 | Zeller et al. | 564/448 |

*Primary Examiner*—Paul F. Shaver
*Attorney, Agent, or Firm*—Alfred D. Lobo; Alan A. Csontos

[57] ABSTRACT

A nitroamine is formed from an aliphatic amine reactant + a nitroalkane + an aldehyde with better conversion, and faster, if the aldehyde is added last, and gradually, so as not to form an alkanolamine intermediate with the aldehyde as in the prior art reactions. In particular, a diamine such as ethylene diamine (EDA) has the unique ability, even among diprimary amines, to react with nitroalkane, to form a salt intermediate to which is added an essentially solvent-free aldehyde such as paraformaldehyde to produce a reaction product consisting essentially of a mixture of (i) a mononitrodialkylenediamine with a disubstituted N-adjacent terminal C atom and (ii) a dinitrotrialkylenediamine with each N-adjacent terminal C atom being disubstituted; and the mixture is obtained in an yield of at least 90 mol %.

6 Claims, No Drawings

SYNTHESIS OF POLYAMINES AND MIXTURE FORMED THEREBY, OF DIPRIMARY POLYALKYLENE POLYAMINES WITH DISUBSTITUTED N-ADJACENT TERMINAL CARBON ATOM(S)

BACKGROUND OF THE INVENTION

This invention is related generally to a novel process for the production of aliphatic polyamines from an aliphatic amine reactant+a nitroalkane+an aldehyde. The term "polyamine" is used to connote a compound with at least one terminal primary amine group and one or more secondary amine groups irrespective of the intermediate alkylene, cycloalkylene, alkyleneimine, or cycloalkyleneimine structure of the compound. Prior art processes have used analogous reactants for the production of aliphatic polyamines by first making an alkanolamine intermediate. Our novel process does not do so. We make a salt intermediate, details of which, and the process are set forth hereinbelow.

Though a primary or secondary amine is an acceptable starting material in both processes, reliance on formation of an alkanolamine intermediate in the prior art process results in a slow reaction and poor yields of nitroamine. Our process relies on the pre-formation of the salt intermediate by protonation of the amine starting material by the nitroalkane, and addition of aldehyde to the salt intermediate has been found to be a more direct route to the corresponding nitroamine, which route is unexpectedly more efficient than the prior art process starting with analogous reactants.

Specifically, this invention relates to the conversion of only aliphatic amine reactants to nitroamines, which are subsequently hydrogenated to aliphatic polyamines. The invention is unrelated to the conversion of arylamines to arylimines which can form nitroamines which in turn may be hydrogenated. Arylimines are stable, particularly under basic conditions, while polyamines are readily polymerized under such conditions, thus are recognized to be distinct from arylimines.

More specifically, this invention relates to the production of polyalkylene polyamines ("PAPA"), particularly those synthesized from other PAPA, and still more specifically to a unique mixture of an acyclic (or noncyclic) mononitroamine and a dinitroamine (referred to herein as "nitroamine mixture" or "first mixture"). From this first mixture is derived a second mixture of (A) a dialkylenetriamine having one disubstituted terminal carbon atom adjacent a primary amine group at one end, and (B) a trialkylenetetramine having two disubstituted terminal C atoms each adjacent a primary amine group at each end (referred to herein as "PAPA mixture"). The term "polyalkylenepolyamine (PAPA)" is specifically used to connote a polyamine with at least three amine groups interconnected with acyclic or cyclic alkylene groups.

A variation of the Mannich reaction has been used in the prior art to produce nitroamines which could then be hydrogenated to produce PAPA. The Mannich reaction involves condensation of a carbonyl compound, for example acetophenone, with formaldehyde and ammonia or a primary or secondary amine. The reaction was modified to improve its selectivity. In the formation of a nitroamine, aqueous formaldehyde is slowly added to an amine (for example, isopropylamine), thus forming the aminoalkanol. 2-nitropropane is then added to the flask at one time and the reaction mixture worked up to yield N-(2-nitroisobutyl)isopropylamine. But successful results have been limited to the use of monoamines which yield mononitro compounds, and then, upon hydrogenation, to diamines. It is evident that the reaction with alkylamines is slow, since the general procedure requires the reaction mixture to stand for several days, and the slow reaction is prone to allow the polymerization of alkylimines formed; where an aryl diamine is used, a more stable arylimine is formed which permits heating the reaction mixture and improving rates. See "Reaction of Primary Aliphatic Amines with Formaldehyde and Nitroparaffins" by Murray Senkus; "id. II. Secondary Amines" by Hal G. Johnson; and, "The Preparation and Reduction of Nitro Amines Obtained from Aromatic Amines, Formaldehyde, and Nitroparaffins" by Hal G. Johnson; J.A.C.S., Vol. 68, 10–17 (Jan 1946).

The order of addition of the reactants, namely aldehyde to amine, and finally the nitroalkane, derived from the work of Henry, Ber., 38, 2027 (1905) which required the formation of the alkanolamine first. Several workers identified in the Senkus article, supra, in later years continued experimentation with the basic reaction but always first added the aldehyde to the amine, and then the nitroalkane when preparing aliphatic polyamines. Because of their predisposition relative to the pre-preparation of the alkanolamine as the intermediate in the preparation of aliphatic polyamines, they were unaware that a change in the order of addition, which change resulted in bypassing the formation of the alkanolamine, would be responsible for a faster reaction and better yields of the desired nitroamine product. Moreover, this change in the order of addition provides better results whether the amine is primary or secondary, alkyl or aralkyl, or an acyclic or cyclic aliphatic amine.

The order of addition was changed by Johnson, supra, in the preparation of N-(2-nitroisobutyl)-aniline from aniline, formalin, and 2-nitropropane, when -he heated one mol aniline, and one mol 2-nitropropane 300 ml methanol as solvent, in the presence of trimethylbenzylammonium hydroxide (TMBAH), then added the formalin. He thus formed the arylimine the stability of which was maintained under basic conditions by addition of the TMBAH, until the arylimine is attacked by the nitropropane to form the nitroamine. Under basic conditions, aliphatic polyamines are polymerized. Thus, the mechanism for the reaction, is quite different from that for an aliphatic amine, and is dictated by the order of addition.

PAPA are commercially produced by the reaction of ethyleneimine and ammonia, a large excess giving mainly ethylenediamine (EDA), and progressively smaller ratios of ammonia to ethyleneimine resulting in the higher homologs, such as diethylenetriamine (DETA), triethylenetetramine (TETA), tetraethylenepentamine (TEPA), and pentaethylenehexamine (PEHA); hexaethylenepentamine (HEPA), or, PAPA are formed as by-products of the reaction of 1,2-dichloropropane (ethylene dichloride) with ammonia (in excess) which yields EDA; or, as byproducts of the reaction af an alkanolamine and ammonia in the presence of hydrogen and a catalyst, as for example described in U.S. Pat. No. 4,014,933. Also produced, along with the acyclic PAPA (such as DETA, linear and branched TETA and higher homologs), are piperazine, aminoethylpiperazine, and cyclic polyethylene polyamines which are not particularly desirable even if they were easy to separate—and they are not.

PAPA, and polyethylene polyamines in particular, are now widely used as emulsifiers, vulcanization accelerators, curing agents for epoxy resins, fungicides, etc. The demand for PAPA has spurred the development of numerous processes for making them, usually by the catalyzed reaction of an alkanolamine, ammonia and an alkyleneamine, disclosed for example in U.S. Pat. Nos. 3,714,259; 3,766,184; 4,036,881; 4,044,053; 4,314,083; and 4,324,917; inter alia, none of which is particularly well-suited for the production of a diprimary triamine with a disubstituted N-adjacent terminal carbon atom, or, a diprimary tetramine with disubstituted terminal N-adjacent carbon atoms. Nor is a process of any of the aforesaid patents stated to be suitable for production of such PAPA. Moreover, each of the patents requires that at least the C atom adjacent the primary amino group of the alkyleneamine have at most only one substituent; and, that the terminal C atom adjacent the terminal N atom of the alkanolamine, likewise have at most only three substituents including the amino group. Evidently, the catalytic reaction does not proceed satisfactorily if the N-adjacent terminal C atom was disubstituted.

One would think that simply substituting a diprimary amine, say EDA, for the isopropylamine used in the modified Mannich reaction referred to hereinabove, would provide a triamine with at least one terminal disubstituted terminal N-adjacent C atom. And it does. Except that it also produces many undesirable byproducts. A diamine such as 1,3-diaminopropane (1,3-PDA) or 1,2-propane diamine (1,2PDA) produces many more cyclic byproducts than does 1,2-ethanediamine.

Similarly, one would expect that substituting a triamine, for example DETA (diethylene triamine), would provide a tetramine with each N-adjacent terminal C atom being disubstituted. And it does. Except that the amount of compound with disubstituted N-adjacent terminal C atoms is formed in so small an amount relative to the unwanted byproducts that separation is not practical, and if recovered would be uneconomical.

Specifically, to make a mixture of particular PAPA through an alkanolamine intermediate, seemed to fly in the face of Cerf de Mauny's rule which states that the number of hydroxymethylamine groups that would react with a nitroalkane is one less than the number of hydrogen atoms linked to the carbon atom to which the nitro group is attached. Because we subscribed to the theory that it was necessary first to form the alaknolamine intermediate, we added aqueous formaldehyde to the organic amine reactant, and the nitroalkane last. Our efforts still met with poor conversions and very slow reaction times until we realized that the key to obtaining better conversion to the nitroamine was adding the aldehyde last, and gradually. It is more preferable to use an essentially solvent-free monoaldehyde, that is an aldehyde with a single —CHO group, and preferably an aldehyde in solid form, such as paraformaldehyde which has a single —CHO group in the repeating unit. By "solvent-free aldehyde" we refer to an aldehyde which is substantially insoluble (less than 5% by weight) in the liquid, typically a lower alkanol, in which the amine and nitroalkane form a salt. When only the organic amine reactant and nitroalkane are present as a mixture along with the salt formed, the amine and nitroalkane liquid is "the liquid" in which the aldehyde is insoluble though it reacts with the salt.

The commercial importance of making the acyclic PAPA which one needs, and at the same time not making a substantial amount of byproducts, cannot be overemphasized. It is therefore serendipitous that a mixture of two highly desirable PAPA can be made with a single, particular diprimary diamine, namely EDA which is premixed with a nitroparaffin to form a salt, which in turn reacts with a solid aldehdye, added gradually under specified conditions; and, that the salt has the unique property of forming the desired mixture with more than 90 mol % yield, and preferably with a yield of less than 5 mol % to unwanted nitroamine byproducts.

SUMMARY OF THE INVENTION

It has been discovered that a nitroamine is formed from an aliphatic amine reactant+a nitroalkane+an aldehyde, with better conversion, and faster, if the aldehyde is added last, and gradually, so as not to form an alkanolamine intermediate with the aldehyde as in the prior art reactions. In the novel process, the deliberate protonation of the amine by the nitroalkane in the first step provides better yield to nitroamines than in the prior art modification of the Mannich reaction, if (i) the aldehyde is added in the second step, and (ii) is solvent-free, and most preferably is solid paraformaldehyde. It is hypothesized that formation of a salt by addition of the nitroalkane to the amine, and the subsequent addition of the aldehyde to the salt, produces the desired nitroamine(s) with much greater purity and much higher conversion and speed than was possible by prior art synthesis.

It has also been discovered that ethylene diamine (EDA) has the unique ability, even among diprimary amines, to react with a nitroalkane, then with an essentially solvent-free, preferably solid aldehyde, to produce a reaction product consisting essentially of a mixture of (i) a mononitrodialkylenediamine with a disubstituted N-adjacent terminal C atom (the structure of this component of the mixture referred to as "compound (I)" is given hereinafter), and (ii) a dinitrotrialkylenediamine with each N-adjacent terminal C atom being disubstituted (this component of the mixture referred to as "compound (II)"); and the reaction product contains less than 10 mol % of nitroamine byproducts (that is, nitro-compounds other than I and II) such as imidazolidines with N,N'-dinitroalkyl substituents.

It has still further been discovered that substitution of a N-adjacent terminal C atom (adjacent the nitro group) in either compound I or compound II, with substituents which may be cyclized with the C atom being in the ring, unexpectedly allows hydrogenation of the $NO_2$ group without forming an appreciable amount of cyclic compounds.

It has specifically been discovered that the ratio of compounds I and II which are formed as a mixture may be controlled by controlling the molar ratio of the components EDA, nitroalkane, and monoaldehyde provided the last named component is added last, is substantially insoluble in the liquid medium in which the prior components form a salt, and the addition is gradual.

Accordingly, it is a specific object of this invention to provide a synthesis for the simultaneous production of a unique mixture of compounds I and II by the noncatalytic reaction of a nitroalkane, EDA, then a solventfree monoaldehyde, for examaple paraforomaldehyde, which reaction results in a yield of less than 10 mol % (based on the mols of all nitroamine reaction products) of products other than compounds I and II; and, thereafter, without separating the desired compounds I and II, hydrogenating the nitroamine reaction product so as to convert the nitro groups to primary amine groups without forming an appreciable amount of unwanted cyclic compounds.

DETAILED DESCRIPTION OF PREFERRED EMBODIMENTS

The preferred embodiment of this invention derives from the discovery that it is both unnecessary and disadvantageous to form an alkanolamine intermediate from which to produce a polyamine which is either (i) a mononitroamine which may be hydrogenated to the corresponding diprimaryamine, or (ii) a dinitroamine which may be hydrogenated to the corresponding alkyleneamine or PAPA.

Pre-preparation of a salt of an aliphatic amine reactant and a nitroalkane (referred to as the 'salt intermediate'), and then adding an essentially solventfree aldehyde, gives better conversion to a desired nitroamine and forms a surprisingly small proportion of unwanted byproducts. Excellent conversion of the nitro groups to primary amine groups is obtained in a subsequent hydrogenation.

By "amine reactant" we refer generally to an aliphatic amine (that is, not an arylamine) which does not have a silicon, phosphorus, boron, or other metal or metal-like elemental component. More specifically we refer to either an aliphatic cyclic monoamine with a secondary amine group in the ring, or an aliphatic acyclic monoamine with a terminal primary or secondary amine group; or, a diprimaryamine with both terminal amine groups being primary, or a PAPA with both primary and secondary amine groups, in which PAPA at least one primary or secondary amine group is a terminal group.

Typical primary monoamines are aralkyl amines such as benzylamine, $C_1$-$C_{20}$ aliphatic amines such as isopropylamine and $C_5$-$C_7$ cycloaliphatic amines such as cyclohexylamine, particularly the lower aliphatic amines, namely $C_1$-$C_6$ such as dimethylaminopropylamine (DMAPA), in each of which the primary amine group is the terminal group.

Preferred are primary diamines, and, polyamines including PAPA with terminal primary amine groups; and, polyamines with one secondary terminal group and one primary terminal group. Most preferred primary diamine is EDA, less preferred being 1,2-PDA, 1,3-PDA, DETA, TETA, TEPA, PEHA, hexamethylenediamine (HMDA) and iminobispropylamine (IBPA). Most preferred polyamine with one secondary and one primary terminal groups is aminoethylpiperazine (AEP).

A typical secondary amine is piperazine which may have a substituent on a ring C or N atom, such as AEP. Other amine reactants are those which have a functionality of at least two (2), so that no tertiary amine group, if present, enters into the reaction.

The amine reactant may be represented by a structure selected from $R^1$—$NH_2$; $H_2N$—$R^{1'}$—$NH_2$; $R^{1'}$—$NH$—$R^{2'}$; $H_2N$—$R^{1'}$—[$NH$—$R^{2'}$]$_n$—$NH_2$; $H_2NCH_2(CH_2NHCH_2)_nCH_2NH_2$; (Aralk)—$NH_2$; (Aralk)—$NH$—$R^1$ and, piperazine, and piperazine having $C_1$-$C_6$ alkyl, and $C_1$-$C_6$-$NH_2$ aminoalkyl substituents on a ring C or N atom; wherein $R^1$ represents H, or $C_1$-$C_{20}$ alkyl, and $R^{1'}$ and $R^{2'}$ represent $C_1$-$C_{20}$ alkylene, that is, having from 1 to about 20 carbon atoms, more preferably $C_1$-$C_6$ lower alkyl, $C_5$-$C_7$ cycloalkyl; (Aralk) represents $C_7$-$C_{20}$ aralklyl; and n is an integer in the range from 0 to 4.

The process for preparing a polyamine comprises, (a) contacting an aliphatic amine reactant with a nitroalkane in predetermined molar proportions to form a liquid mixture and a salt intermediate at a temperature above the freezing point of the liquid mixture and below that deleterious to the salt, preferably in the presence of an inert liquid reaction medium, preferably a lower primary or secondary alcohol which forms a solution of said salt;

(b) gradually adding an essentially solvent-free monoaldehyde to the solution to form a reaction mixture in which the nitroalkane is converted to a nitroamine with a a yield of a minor molar amount (less than 50 mol %) of unwanted nitroamine byproducts, the yield being based on the amount of nitroalkane reacted; thereafter, (c) without separating the reaction products from the reaction mixture, contacting the reaction mixture with hydrogen under sufficient pressure and temperature and in the presence of a catalytically effective amount of metal hydrogenation catalyst; and, (d) recovering said polyamine in a yield greater than 50 mol % based on the stoichiometric amount of nitroalkane converted, and preferably greater than about 90 mol % converted.

Preferred temperature for the formation of the salt is in the range from 0° C. to 50° C., most preferred being about ambient temperature. The pressure is not critical and may be subatmospheric or superatmospheric depending upon the temperature chosen for the initial reaction. After formation of the salt intermediate, the reaction After formation of the salt intermediate, the reaction temperature with the aldehdye is 20°-80° C., preferably 40°-60° C. The surprisingly small amount of unwanted nitroamine by-products formed makes it unnecessary to separate the desirable nitroamines before they are hydrogenated, which separation is a hazardous undertaking. The conditions for hydrogenation are in the range from about 15° C. to about 50° C. and a pressure in the range from about 50 psig to about 500 psig with Raney nickel for a period of time sufficient to hydrogenate essentially all the nitro groups in the nitroamine compounds. The reaction mixture may be post-hydrogenated for a period of 10-30 min, for safety reasons.

In addition to changing the order of addition of the aldehyde to avoid formation of the alkanolamine intermediate, it is critical that an aldehyde be used which contains less than 5% by wt of a solvent for the aldehyde, more preferably less than 1% by wt, and most preferably solid paraformaldehyde which is essentially insoluble in water. For example, the presence of water as the solvent for formaldehyde produces an unacceptably high percentage of unwanted cyclic and polymeric byproducts. However, the acyclic $C_1$-$C_6$ lower alkyl aldehydes are substantially insoluble in lower alkanols, such as isopropanol, which alkanols serve a dual function as solvent for the salt intermediate, and as inert liquid reaction medium.

In the prior art, a primary monoamine is converted to the nitroamine as follows:

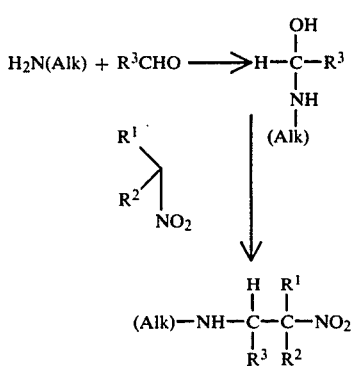

wherein (Alk) represents $C_1$–$C_{20}$ alkyl, and preferably $C_1$–$C_6$ lower alkyl.

In our invention, the aldehyde is added last, as follows:

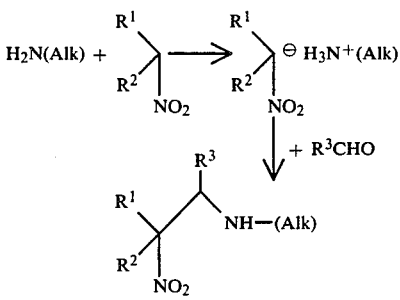

By adding the aldehyde to the salt intermediate, a nitroamine is formed in better yield than that obtained in the prior art. Upon hydrogenation, the nitroamine is converted to the polyamine with essentially no decrease in yield.

In the prior art, a diamine with terminal primary amine groups is converted to the nitroamine as follows:

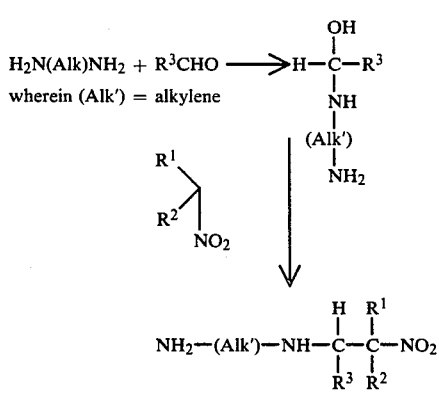

In our invention, the aldehyde is added last, as follows:

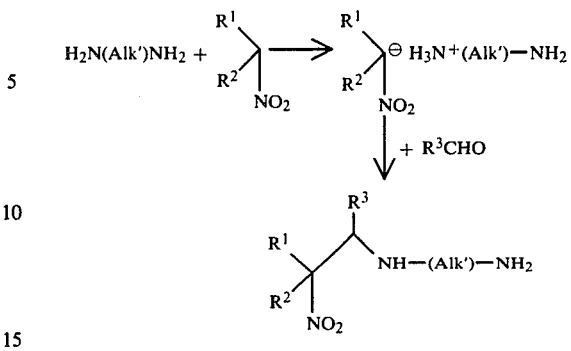

As before, by adding the aldehyde to the salt intermediate, a nitroamine is formed in better yield than that obtained in the prior art. Upon hydrogenation, the nitroamine is converted to the polyamine with terminal primary amine groups, with essentially no decrease in yield.

Though the general process may be used to produce any polyamine from an aralkylamine, aliphatic or cycloaliphatic alkyleneamine rectant, the process is most advantageously used to react the lower alkylenediamines such as EDA, DETA, TETA, 1,2-PDA and 1,3-PDA, with a nitroalkane, then an aldehyde, to produce a mixture of nitroamines substantially free of unwanted nitroamine byproducts; and, this mixture, without separation of the reaction products, may be hydrogenated in the presence of a catalytically effective amount of Raney Ni to form a preselected mixture of polyalkylenepolyamines (PAPA) in a predetermined ratio, under surprisingly mild conditions, again substantially free of unwanted PAPA byproducts. Most preferred is EDA.

In the best mode, the composition of this invention is a mixture of a diethylenetriamine (compound A) and a triethylenetetramine (compound B) derived by reacting a EDA with a nitroalkane, then with a finely divided solid aldehyde to produce a mixture of a mononitrodiethylenediamine (I) and a dinitrotriethylenediamine (II) which are branched polyethylene nitroamines. These compounds (I) and (II), upon hydrogenation in the presence of catalyst, yield the mixture of compounds A and B which are branched polyethylene polyamines. The sequence of reactions is as follows:

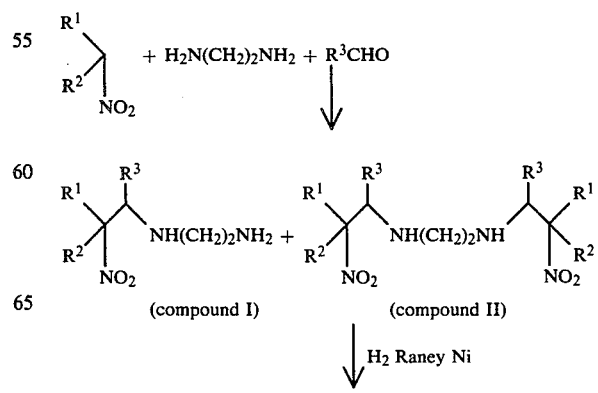

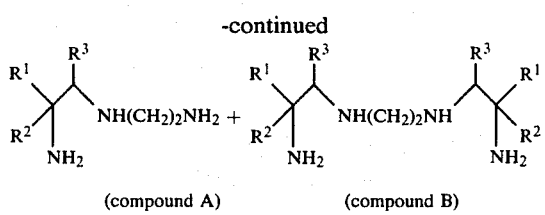

(compound A)    (compound B)

wherein, $R^1$ and $R^2$ have the same connotation as that given hereinbefore, and in addition represent, $C_2$-$C_{20}$ alkylether $R_4$—O—$R_5$ wherein $R_4$ and $R_5$ are each alkyl, $C_2$-$C_{20}$ alkylaminoalkyl $R_5R_6$—N—$R_7$ wherein $R_5$, $R_6$, and $R_7$ are each alkyl and, in addition, only one of which may be H; and $R^1$ together with $R^2$ may be cyclized, forming a ring with from about 5 to about 7 C atoms;

$R^3$ represents H, $C_1$-$C_{20}$ alkyl, preferably $C_1$-$C_6$ lower alkyl, $C_6$ aryl, and, $C_4$-$C_7$ cycloalkyl; the amount of unwanted nitroamine byproducts formed, that is, other than compounds (I) and (II) is generally less than 50 mol %, and more preferably, no more than 10 mol % of the total amount of nitroamines formed; and, the yield of PAPA byproducts formed, other than compounds A and B, is less than 10 mol % of the total amount of PAPA formed.

Most preferred nitroalkanes are $C_3$-$C_9$ nitroparaffins, in which the nitro group is attached to other than the lC atom, for example 2-nitropropane, and $C_5$-$C_7$ nitrocycloalkanes such as nitrocyclohexane.

Preferred aldehydes are propionaldehyde, and butyraldehyde, most preferred being paraformaldehyde.

Though 1,2-PDA, 1,3-PDA, DETA, TETA and even higher homologous polyamines will provide useful nitroamines, in better yields and at faster rates than the prior art processes, only ethylenediamine reacts with the foregoing aldehydes and nitroalkanes with the desired specificity, confirming the unpredictability of the various reactions which are expected to produce PAPA, and lending substance to the contradictions in the findings of Henry, Mousset and Cerf referred to in the Senkus article supra.

A typical preparation requires formation of a salt intermediate from a mixture of the nitroalkane (NA) and ethylenediamine (EDA) to which mixture is gradually added the solvent-free aldehyde (A), with stirring, and the reaction proceeds smoothly at a temperature in the range from about 0° C. to about 50° C. The precise rate at which the aldehyde is added is not narrowly critical and will depend upon the size of the charge of EDA and NA in the reactor. Too fast a rate will result in the temperature exceeding 50° C., which is to be avoided, and the concomitant formation of an undesirably large proportion by wt of byproducts. The precise rate can be determined with a little trial and error such as one skilled in the art will expect to undertake to make the determination within the parameters set forth.

The compound (I) is named N-(2-methyl-2-nitropropyl)-1,2-ethanediamine.

The compound (II) is named N,N'-bis(2-methyl-2-nitropropyl)-1,2-ethanediamine.

The compound A is named $N^1$-(2-aminoethyl)-2-methyl-1,2-propanediamine.

The compound B is named $N^1,N^{1\prime}$-ethanediylbis[2-methyl-1,2-propanediamine].

If an equimolar ratio of the reactants (that is, EDA:NA:A = 1:1:1) is used, about equimolar amounts of the mononitrodiethylenediamine (I) and the dinitrotriethylenetriamine (II) are formed; if the ratio is 2:1:1 then a minor molar proportion of the (II) is formed, the major component of the reaction being the (I); if the ratio is 3:1:1 then in excess of 75% (molar basis) of (I) is formed which may amount to as much as 95 mol % of all the nitroamines, with only about 1 mol % of (II); if two mols of the nitroalkane are used for each mol of aldehyde and ethylenediamine, that is the ratio of EDA:NA:A = 1:2:1, then more (II) than (I) is formed. A larger excess of the nitroalkane produces more than 75% of (II) which may amount to as much as 95 mol % of all the nitroamines, with only about 1% of (I). Thus, since essentially all nitro groups are hydrogenated, depending upon the ratio of components chosen, the molar ratio of compounds A and B in the mixture thereof will range from about 1:95 to about 95:1. In any of the foregoing cases, less than 10 mol % of the reaction product consists of other nitro compounds than A and B, particularly unwanted cyclic compounds.

The particular identification of the byproduct PAPA formed is difficult because they are produced in relatively small quantities which makes their separation and identification a major undertaking. Gummy materials isolated appear to be polymeric amines; and, still others give characteristic spectra of cyclic PAPA.

The nitroamines in the reaction product are hydrogenated to the corresponding polyamines without separation of the components, so that if the first reaction is carried out in a pressure vessel, the reaction mixture can be hydrogenated without transferring the mixture, thus minimizing the risk of explosion. Hence the process is referred to a "one-pot synthesis for PAPA". If desired, the reaction mixture may be diluted with a lower alkanol, preferably isopropanol, and the solution hydrogenated as described hereinabove to convert the nitro groups on essentially all the nitroamines to primary amine groups For preparing the particular mixture of a diethylenetriamine and a triethylenetetramine, the processcomprises, (i) mixing a nitroalkane (NA) having the structure

wherein, $R^1$ and $R^2$ have the same connotation as given above, with ethylenediamine (EDA) in a preselected ratio of EDA:NA in the range from 4:1 to 1:4, to form an EDA/NA mixture including a salt intermediate;

(ii) gradually adding to the EDA/NA mixture an essentially solvent-free aldehyde having the formula $R^3$CHO in at least an equimolar amount of the lesser of EDA or NA, wherein, $R^3$ has the same connotation as given hereinabove, (iii) maintaining the reaction temperature after forming the salt intermediate in the range from about 20° C. to about 80° C. while stirring; whereby the amount of nitroamine byproducts formed, other than compounds (I) and (II), is less than 10 mol % of the total amount of nitroamines formed; and, (iv) contacting the mixture of (I) and (II) with hydrogen in the presence of Raney Ni at a temperature in the range from about 15° C. to about 50° C. and a pressure in the range from about 50 psig to about 500 psig for a period of time sufficient to hydrogenate essentially all the nitro groups in said compounds; whereby the amount of polyamine byproducts formed, other than compounds A and B, is less than 10 mol % of the total amount of polyamines formed.

The hydrogenated solution recovered is filtered and the filtrate distilled to recover the alkanol under any convenient and economical conditions, preferably under slightly reduced pressure. Most preferred is isopropanol which is stripped under reduced pressure at a temperature in the range from about 40°-45° C. along with water and unreacted ethylenediamine leaving a residue which does not require further drying, and containing the desired PAPA with less than 10 mol % of other PAPA.

The mixture of compounds A and B can be tailored for any specific application based on their cumulative properties for example as emulsifiers, or as curing agents for epoxy compounds, or as precursors for the production of 2-piperazinone compounds which are useful as uv-light stabilizers as disclosed in U.S. Pat. No. 4,480,092 the disclosure of relevant portions of which is incorporated by reference thereto as if fully set forth herein.

The following illustrative examples provide details for the preparation of a mixture of specific PAPA, namely $N^1$-(2-aminoethyl)-2-methyl-1,2-propanediamine, and, $N^1,N^{1'}$-ethanediylbis[2-methyl-1,2-propanediamine].

EXAMPLE 1

In a three-necked round-bottom 500 ml flask equipped with a condenser, thermometer and mechanical stirrer was charged 89 g (1 mol) 2-nitropropane (NA), which was cooled by placing the flask in an ice-bath. 180 g (3 mols) EDA was added slowly to form the salt intermediate while keeping the temperature below 20° C. After addition of all the EDA, 30.9 g of powder paraformaldehyde is added slowly while stirring so that all is added over a period of 30 min. The reaction mixture is kept stirred at room temperature until all the the NA is reacted. It is found that in excess of 90 mol % of the NA is converted to nitroamines (I) and (II).

The reaction mixture is transferred to a 1 liter stirred pressure reactor, and 20 g Raney Ni, and 250 ml i-PrOH are added. The reactor is purged with nitrogen and pressured with $H_2$ starting at 150 psig and 40° C., and ending at 500 psig and 120° C. until, after about 6 hr, there is no further uptake of $H_2$. GC analysis indicates that about 10 times as much compound A is formed, than compound B.

In a manner analogous to that described hereinabove 160.2 g (1.8 mols) NA and 120 g (2 mols) EDA formed the salt in 250 ml i-PrOH to which was added 55.5 g (1.8 mols) powder paraformaldehyde. The reaction product was hydrogenated as described hereinabove and after about 7 hr about twice as much compound A was formed as compound B.

Repetition of the foregoing reaction with varying molar ratios and different conditions of temperature and pressure provides a preselected ratio of compounds A and B in the range of ratios set forth hereinabove.

EXAMPLE 2

118 g (2 mols) of isopropylamine are slowly added to 178 g (2 mols) 2-nitropropane placed in a flask in an icebath and the temperature kept in the 17°-20° C. range while the salt intermediate is formed. Thereafter 64 g (2 mols) of paraformaldehyde are added slowly over a period of 30 min. while stirring, and the stirring continued for 4 hr. Upon analysis it is found that more than 90 mol % of the 2-nitropropane was converted to N-(2-nitroisobutyl)-isopropylamine b.p. 85° C. at 10 mm.

The foregoing procedure for preparing the nitroamine is repeated and 250% ml of i-PrOH are added to the mixture which is transferred to a pressure vessel for hydrogenation under conditions essentially the same as those described in Example 1 hereinabove. In excess of 90 mol % conversion of the nitroamine to N-(2-aminoisobutyl)isopropylamine (b.p. 147° C.) is obtained.

EXAMPLE 3

The foregoing procedure is also used to prepare nitrodiamines from primary amines and primary nitroparaffins to which is added a solvent-free aldehyde.

. In a manner analogous to that described hereinabove, 1 mol of nitroethane is added slowly to 2 mols of isopropylamine to form the salt intermediate, and thereafter 2 mols of paraformaldehyde are slowly added to the salt with stirring which is continued for 4 hr. The conversion of the nitroethane to 2-nitro-2-methyl-1,3-di(isopropylamino)propane is in excess of 90 mol %. The reaction mixture is then diluted with 250 ml of i-PrOH and hydrogenated in a manner analogous to that described hereinabove, to yield 2-amino-2-methyl-1,3-di(isopropylamino)propane the conversion of which is in excess of 90 mol % based on the nitroethane charged.

From the foregoing examples it is evident that both nitromonoamines and nitrodiamines may be prepared more quickly and efficiently from primary or secondary alkylamines and primary nitroparaffins, by first forming the salt intermediate in an initial reaction, and adding aldehyde gradually and last, in a subsequent reaction, preferably in the presence of a lower primary or secondary alkanol which is not a solvent for the aldehyde.

We claim:
1. A process for preparing a polyamine comprising,
   (i) mixing a nitroalkane (NA) having the structure

wherein, $R^1$ and $R^2$ represent H, $C_1$–$C_{20}$ alkyl, $C_5$–$C_7$ cycloalkyl, $C_2$–$C_{20}$ alkylether, $C_2$–$C_{20}$ alkylaminoalkyl, and $R^1$ together with $R^2$ may be cyclized forming a ring with from about 5 to about 7 C atoms;

with an aliphatic amine reactant to form a mixture containing a salt intermediate, said amine reactant being selected from the group consisting of piperazine, substituted piperazines having substituents on the N or C atoms in the ring; an acyclic monoamine having a terminal primary amine group; a diprimaryamine with both terminal amine groups being primary; and, a polyalkylene polyamine (PAPA) with both primary and secondary amine groups, in which PAPA at least one primary or secondary amine group is a terminal group;

(ii) gradually adding to said mixture an essentially solvent-free aldehyde having the formula $R^3CHO$ in at least an equimolar amount of the lesser of EDA or NA, wherein, $R^3$ represents represents H, $C_1$–$C_{20}$ alkyl, preferably $C_1$–$C_6$ lower alkyl, $C_6$ aryl, and, $C_4$–$C_7$ cycloalkyl;

(iii) maintaining the temperature in the range from about 0° C. to about 50° C. while stirring to form a reaction mixture containing a nitroamine having a terminal nitro group; and, (iv) contacting said reaction mixture with hydrogen in the presence of a catalytically effective amount of Raney Ni at a temperature in the range from about 15° C. to about 50° C. and a pressure in the range from about 50 psig to about 500 psig for a period of time sufficient to hydrogenate essentially all the nitro groups in said compounds;

whereby the yield of said polyamine is greater than 10 mol % of the nitroalkane converted to polyamines.

2. The process of claim 1 wherein said amine reactant is selected from the group consisting of $R^1$—$NH_2$; $H_2N$—$R^{1'}$—$NH_2$; $R^{1'}$—$NH$—$R^{2'}$; $H_2N$—$R^{1'}$—[NH—$R^{2'}]_n$—$NH_2$; $H_2NCH_2(CH_2NHCH_2)_nCH_2NH_2$; (Aralk)—$NH_2$; (Aralk)—$NH$—$R^1$ and, piperazine, and piperazine having $C_1$–$C_6$ alkyl, and $C_1$–$C_6$-$NH_2$ aminoalkyl substituents on a ring C or N atom; wherein $R^{1'}$ and $R^{2'}$ represent alkylene and $C_5$–$C_7$ cycloalkylene; (Aralk) represents $C_7$–$C_{20}$ aralklyl; and n is an integer in the range from 0 to 4.

3. A process for preparing a mixture of polyalkylenepolyamines (PAPA) including a dialkylenetriamine and a trialkylenetetramine comprising, (a) contacting an aliphatic amine reactant with a nitroalkane in predetermined molar proportions at a temperature in the range from 0° C. to about 50° C. and ambient pressure to form a mixture containing a salt intermediate;

(b) gradually adding an essentially solvent-free aldehyde to said mixture to maintain a reaction temperature in the range from about 20° C. to about 80° C. to form a reaction mixture containing a nitroamine; thereafter, (c) without separating the reaction products from the reaction mixture, contacting said reaction mixture with hydrogen under sufficient pressure and temperature and in the presence of a catalytically effective amount of Raney nickel for a period of time long enough to convert all nitro groups to primary amine groups; and, (d) recovering said mixture of PAPA from the reaction mixture which contains less than 10 mol % of unwanted amine byproducts.

4. The process of claim 3 wherein step (a) is carried out in the presence of an inert liquid reaction medium in which said aldehyde is essentially insoluble, but which liquid forms a solution of said salt.

5. The process of claim 4 wherein a mixture of nitroamines is formed consisting essentially of a dialkylenetriamine (compound I) and a trialkylenetetramine (compound II) having the structures

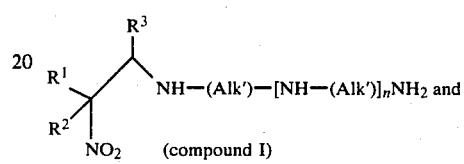

(compound I)

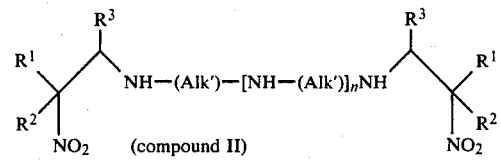

(compound II)

wherein (Alk') represents $C_1$–$C_{20}$ alkylene and $C_5$–$C_7$ cycloalkylene; and, n is an integer in the range from 0 to 4.

6. The process of claim 5 wherein said amine reactant is ethylene diamine (EDA), said nitroalkane (NA) is 2-nitropropane, said aldehyde (A) is paraformaldehyde, and the ratio of said EDA:NA:A is in the range from about 4:1:1 to about 1:4:1.

* * * * *

UNITED STATES PATENT AND TRADEMARK OFFICE
CERTIFICATE OF CORRECTION

PATENT NO. : 4,698,446

DATED : October 6, 1987

INVENTOR(S) : JOHN T. LAI and PYONG N. SON

It is certified that error appears in the above—identified patent and that said Letters Patent is hereby corrected as shown below:

Column 12, Line 8; "is repeated and 250% ml of i-PrOH" should read -- is repeated and 250 ml of i-PrOH -- .

Signed and Sealed this

Nineteenth Day of July, 1988

Attest:

DONALD J. QUIGG

Attesting Officer

Commissioner of Patents and Trademarks